US012702542B2

(12) United States Patent
Wu

(10) Patent No.: US 12,702,542 B2
(45) **Date of Patent: *Aug. 11, 2026**

(54) FOLDING DEVICE FOR INTRAOCULAR LENS INJECTOR

(71) Applicant: Alcon Inc., Fribourg (CH)

(72) Inventor: Yinghui Wu, Cedar Hill, TX (US)

(73) Assignee: Alcon Inc., Fribourg (CH)

( * ) Notice: Subject to any disclaimer, the term of this patent is extended or adjusted under 35 U.S.C. 154(b) by 467 days.

This patent is subject to a terminal disclaimer.

(21) Appl. No.: 18/058,045

(22) Filed: Nov. 22, 2022

(65) Prior Publication Data

US 2023/0078517 A1 Mar. 16, 2023

Related U.S. Application Data

(62) Division of application No. 16/688,252, filed on Nov. 19, 2019, now Pat. No. 11,534,292.

(60) Provisional application No. 62/781,709, filed on Dec. 19, 2018.

(51) Int. Cl.
*A61F 2/16* (2006.01)

(52) U.S. Cl.
CPC ............ *A61F 2/1678* (2013.01); *A61F 2/167* (2013.01); *A61F 2002/1683* (2013.01)

(58) Field of Classification Search
CPC .................... A61F 2/1678; A61F 2/167; A61F 2002/1683; A61F 9/0008
See application file for complete search history.

(56) References Cited

U.S. PATENT DOCUMENTS

| | | | |
|---|---|---|---|
| 5,190,552 A | 3/1993 | Kelman | |
| 5,304,182 A | 4/1994 | Rheinish | |
| 2003/0209452 A1 | 11/2003 | Mitomo et al. | |
| 2008/0039862 A1 | 2/2008 | Tran | |
| 2011/0144654 A1 | 6/2011 | Isaacs et al. | |
| 2013/0304078 A1* | 11/2013 | Issacs | A61F 2/167 606/107 |
| 2016/0331587 A1* | 11/2016 | Yamada | A61F 2/1678 |
| 2017/0119522 A1 | 5/2017 | Auld et al. | |
| 2019/0254812 A1 | 8/2019 | Maroschek | |

FOREIGN PATENT DOCUMENTS

| | | |
|---|---|---|
| EP | 2873391 A1 | 5/2015 |
| IL | 160381 A | 7/2004 |
| IN | 201847013724 A | 4/2018 |
| IT | MI930147 A1 | 7/1994 |
| JP | 2015171529 A | 10/2015 |
| WO | 9410912 A1 | 5/1994 |
| WO | 2018006889 A2 | 1/2018 |
| WO | 2018221434 A1 | 12/2018 |

* cited by examiner

*Primary Examiner* — Tan-Uyen T Ho
*Assistant Examiner* — Chima U Igboko

(57) ABSTRACT

Intraocular lens (IOL) folding devices and methods of folding an IOL or components thereof are disclosed.

9 Claims, 10 Drawing Sheets

FOLDING DEVICE FOR INTRAOCULAR LENS INJECTOR

TECHNICAL FIELD

The present disclosure relates to systems, apparatuses, and methods for intraocular lens injectors and, particularly, to systems, apparatuses, and methods for folding intraocular lenses prior to delivery into an eye of a patient.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape, and length of the eye, and the shape and transparency of the cornea and lens. When trauma, age, or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial intraocular lens ("IOL").

Many cataractous lenses are removed by a surgical technique called phacoemulsification. During this procedure, an opening is made in the anterior capsule of an eye and a phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced with an IOL.

The IOL may be injected into the eye through a small incision, sometimes the same incision used to remove the diseased lens. An IOL injector may be used to deliver an IOL into the eye. In order to minimize the size of the incision made in the eye, and thereby decrease patient recovery time, the IOL may be folded or rolled into a smaller configuration for implantation using the IOL injector.

SUMMARY

According to first aspect, the present disclosure relates to an intraocular lens (IOL) folding device. The IOL folding device includes a folding body having a first side that has a first slot, and a second side disposed opposite the first side and having a second slot. The folding body also has a center compartment adapted to house an IOL having a first haptic, a second haptic and a base having a first edge and a second edge. The IOL folding device has a first lever disposed within the folding body and adapted to contact and apply force against the first haptic of the IOL, a second lever disposed within the folding body and adapted to contact and apply force against the second haptic of the IOL, a third lever disposed within the folding body and adapted to contact and apply force against the first edge of the IOL base, and a fourth lever disposed within the folding body and adapted to contact and apply force against the second edge of the IOL base. The IOL folding device has a first side actuator disposed within and extending horizontally through the first slot and includes a first side actuator contact surface adapted for application of manual force, a first link extending horizontally through the slot on the first side of the folding body, the first link contiguous with the first side actuator contact surface and rotatably coupled to the first lever and adapted to horizontally rotate the first lever in response to application of manual force to the first actuator contact surface to apply force to the first haptic of the IOL sufficient to press the first haptic against the base of the IOL, and a third link extending horizontally through the slot on the first side of the folding body, the third link contiguous with the first side actuator contact surface adapted to engage the third lever to vertically rotate the third lever in response to application of manual force to the first actuator contact surface to apply force to the first edge of the IOL sufficient to fold the base of the IOL. The IOL folding device also has a second side actuator disposed within and extending horizontally through the second slot and including a second side actuator contact surface adapted for application of manual force. The IOL folding device also has a second link extending horizontally through the slot on the second side of the folding body, the second link contiguous with the second side actuator contact surface and rotatably coupled to the second lever and adapted to horizontally rotate the second lever in response to application of manual force to the second actuator contact surface to apply force to the second haptic of the IOL sufficient to press the second haptic against the base of the IOL. The IOL folding device also has a third link extending horizontally through the slot on the second side of the folding body the third link contiguous with the second side actuator contact surface adapted to engage the fourth lever to vertically rotate the fourth lever in response to application of manual force to the second actuator contact surface to apply force to the second edge of the IOL sufficient to fold the base of the IOL.

According to second aspect, the present disclosure relates to an intraocular lens (IOL) folding device. The IOL folding device includes a circular folding body having a center compartment adapted to house an IOL having a first haptic, a second haptic, and a base having a first edge and a second edge. The circular folding body has a rotatable cover disposed over the center compartment of the folding body, the rotatable cover having a first slot, a second slot, a third slot, and a fourth slot. The IOL folding device has a first lever disposed within the circular folding body and includes a first peg extending through the first slot and a first pivot point, the first lever adapted for, when the rotatable cover is rotated, the first peg to slidingly interact with the first slot to rotate the first lever around the first pivot point to contact and apply force to the first haptic of the IOL sufficient to press the first haptic against the base of the IOL. The IOL folding device also has a second lever disposed within the circular folding body and includes a second peg extending through the second slot and a second pivot point, the second lever adapted for, when the rotatable cover is rotated, the second peg to slidingly interact with the second slot to rotate the second lever around the second pivot point to contact and apply force to the second haptic of the IOL sufficient to press the second haptic against the base of the IOL. The IOL folding device also has a third lever disposed within the circular folding body and includes a third peg extending through the third slot and a third pivot point, the third lever adapted for, when the rotatable cover is rotated, the third peg to slidingly interact with the third slot to rotate the third lever around the third pivot point to contact and apply force to the first edge of the IOL sufficient to fold the base of the IOL. The IOL folding device also has a fourth lever disposed within the circular folding body and includes a fourth peg extending through the fourth slot and a fourth pivot point, the fourth lever adapted for, when the rotatable cover is rotated, the fourth peg to slidingly interact with the fourth slot to rotate the fourth lever around the fourth pivot point to contact and apply force to the second edge of the IOL sufficient to fold the base of the IOL.

According to a third aspect, the present disclosure relates to an intraocular lens (IOL) injector. The IOL injector has an injector body and a nozzle having a hollow interior disposed on a distal end of the injector body. The IOL injector also has a plunger adapted to reciprocate within the injector body and to contact and apply force to an IOL disposed in the IOL injector, the IOL having a first haptic, a second haptic; and a base having a first edge and a second edge. The IOL injector also has a folding body. The folding body has a center compartment adapted to house the IOL, a first lever disposed within the folding body and adapted to contact and apply force against the first haptic of the IOL sufficient to press the first haptic against the base of the IOL, a second lever disposed within the folding body and adapted to contact and apply force against the second haptic of the IOL sufficient to press the second haptic against the base of the IOL, a third lever disposed within the folding body and adapted to contact and apply force against the first edge of the IOL base sufficient to fold the base of the IOL, and a fourth lever disposed within the folding body and adapted to contact and apply force against the second edge of the IOL base sufficient to fold the base of the IOL.

The various aspects may include one or more of the following features. The intraocular lens folding device may include a delivery channel disposed below the folding body and extending from a proximal end of the folding body to a distal end of the folding body, the delivery channel adapted to receive an IOL folded into a delivery configuration and adapted to align with a delivery channel in a body and a nozzle of an IOL injector. The first and second links may rotate the first and second levers prior to the third and fourth links engaging the third and fourth levers. The intraocular lens folding device may include the IOL disposed within the center compartment. The IOL may have an optic disposed within the base. The first side actuator and the second side actuator may be adapted for simultaneous application of manual force. The intraocular lens folding device may include a second rotatable cover disposed above and coupled to the first rotatable cover. In the IOL injector, the folding body may include a first side having a first slot, a second side disposed opposite the first side and having a second slot, a first side actuator disposed within and extending horizontally through the first slot, wherein the first side actuator has: a first side actuator contact surface adapted for application of manual force, a first link extending horizontally through the slot on the first side of the folding body, the first link contiguous with the first side actuator contact surface and rotatably coupled to the first lever and adapted to horizontally rotate the first lever in response to application of manual force to the first actuator contact surface to apply force to the first haptic of the IOL sufficient to press the first haptic against the base of the IOL; the folding body may have a third link extending horizontally through the slot on the first side of the folding body the third link contiguous with the first side actuator contact surface adapted to engage the third lever to vertically rotate the third lever in response to application of manual force to the first actuator contact surface to apply force to the first edge of the IOL sufficient to fold the base of the IOL; a second side actuator disposed within and extending horizontally through the second slot and having: a second side actuator contact surface adapted for application of manual force, a second link extending horizontally through the slot on the second side of the folding body, the second link contiguous with the second side actuator contact surface and rotatably coupled to the second lever and adapted to horizontally rotate the second lever in response to application of manual force to the second actuator contact surface to apply force to the second haptic of the IOL sufficient to press the second haptic against the base of the IOL; and a third link extending horizontally through the slot on the second side of the folding body the third link contiguous with the second side actuator contact surface adapted to engage the fourth lever to vertically rotate the fourth lever in response to application of manual force to the second actuator contact surface to apply force to the second edge of the IOL sufficient to fold the base of the IOL. In the IOL injector, the first and second links may rotate the first and second levers prior to the third and fourth links engaging the third and fourth levers. In the IOL injector, the first side actuator and the second side actuator may be adapted for simultaneous application of manual force. In the IOL injector, the folding body may be a circular folding body having a rotatable cover disposed over the center compartment of the folding body, the rotatable cover including a first slot, a second slot, a third slot, and a fourth slot, wherein: the first lever is disposed within the circular folding body and includes a first peg extending through the first slot and a first pivot point, the first lever is adapted for, when the rotatable cover is rotated, the first peg to slidingly interact with the first slot to rotate the first lever around the first pivot point to contact and apply force to the first haptic of the IOL sufficient to press the first haptic against the base of the IOL; the second lever is disposed within the circular folding body and comprises a second peg extending through the second slot and a second pivot point, the second lever is adapted for, when the rotatable cover is rotated, the second peg to slidingly interact with the second slot to rotate the second lever around the second pivot point to contact and apply force to the second haptic of the IOL sufficient to press the second haptic against the base of the IOL; the third lever is disposed within the circular folding body and includes a third peg extending through the third slot and a third pivot point, the third lever is adapted for, when the rotatable cover is rotated, the third peg to slidingly interact with the third slot to rotate the third lever around the third pivot point to contact and apply force to the first edge of the IOL sufficient to fold the base of the IOL; and the fourth lever is disposed within the circular folding body and includes a fourth peg extending through the fourth slot and a fourth pivot point, the fourth lever is adapted for, when the rotatable cover is rotated, the fourth peg to slidingly interact with the fourth slot to rotate the fourth lever around the fourth pivot point to contact and apply force to the second edge of the IOL sufficient to fold the base of the IOL. In the IOL injector, the circular folding body may include a second rotatable cover disposed above and coupled to the first rotatable cover. In the IOL injector, the injector body may have a delivery channel disposed below the folding body and extending from a proximal end of the folding body to a distal end of the folding body, the delivery channel adapted to receive an IOL folded into a delivery configuration and align with a delivery channel in the injector body and nozzle. In the IOL injector, the circular folding body may include the IOL disposed within the center compartment. In the IOL injector having the circular folding body, the IOL may include an optic disposed within the base.

BRIEF DESCRIPTION OF THE DRAWINGS

For a more complete understanding of the present disclosure, reference is now made to the following description, taken in conjunction with the accompanying drawings, which are not to scale, and in which.

DETAILED DESCRIPTION

Figure 1:
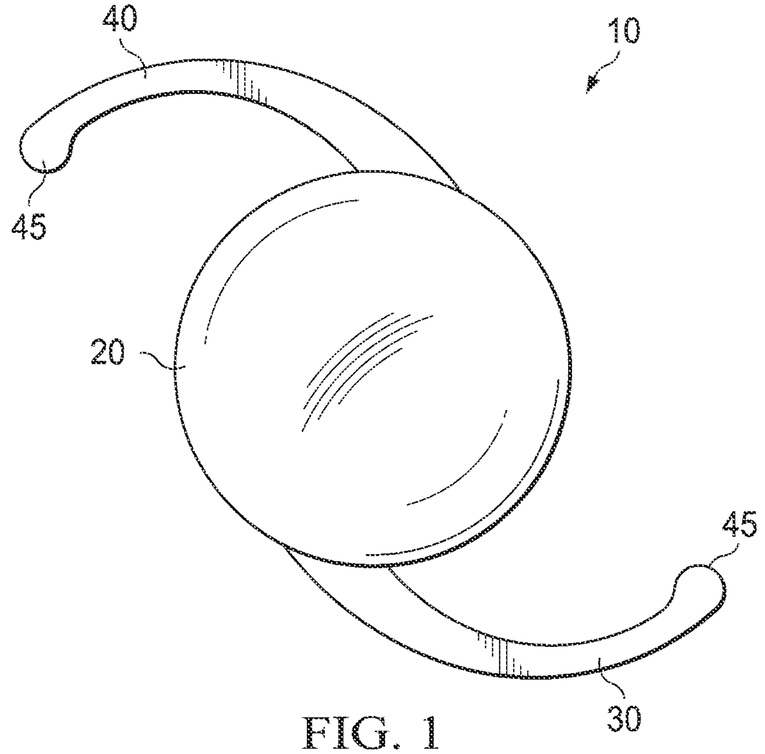
FIG. 1 shows an example intraocular lens.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

A recent design for an IOL includes of a hollow base with two protruding haptic arms, and an optic that sits in the base. This design has a more complex folding behavior than single piece IOLs. For example, most conventional single piece IOL injectors advance the IOL by directly applying forces to the edge of the IOL optic or haptic. This technique is not well adapted for a hollow base design because the base could collapse if an external force is applied to the edge of the base. Furthermore, traditionally the IOL is manually loaded and folded into an injector by picking up the IOL using forceps and placing it into a folding chamber. This manual process creates the potential for damaging the IOL object, user error in loading the IOL, and errors in ensuring all components remain sterile during the process. Therefore, the present disclosure provides folding mechanisms that may be compatible with IOLs having a hollow base, and possibly also other multi-part IOLS or conventional single-piece IOLs. The folding mechanisms may also ensure that the IOL remains sterile and intact until implantation in the patient's eye.

The present disclosure relates to systems, apparatuses, and methods for folding an IOL and delivering the folded IOL into an eye. FIG. 1 shows an example IOL 10. The IOL 10 is a one-piece IOL that includes a optic 20, a leading haptic 30, and a trailing haptic 40. Each of the haptics 30 and 40 has a freely extending end 45.

In some implementations, the IOL 10 may be a one-piece IOL. That is, in some implementations, the IOL 10 may include an optic 20 and haptics 30 and 40, as shown in FIG. 1. In some implementations, the optic 20 and the haptics 30 and 40 may be integrally formed out of a single piece of material. In other implementations, the optic 20 may be formed out of one piece of material; the haptics 30 and 40 may be formed out of another piece of material; and the optic 20 and the haptics 30 and 40 may be coupled together prior to delivery into an eye. In some instances, the optic 20 and haptics 30 and 40 may be fixedly secured to each other prior to insertion into an IOL injector and delivered into an eye.

Figure 10:
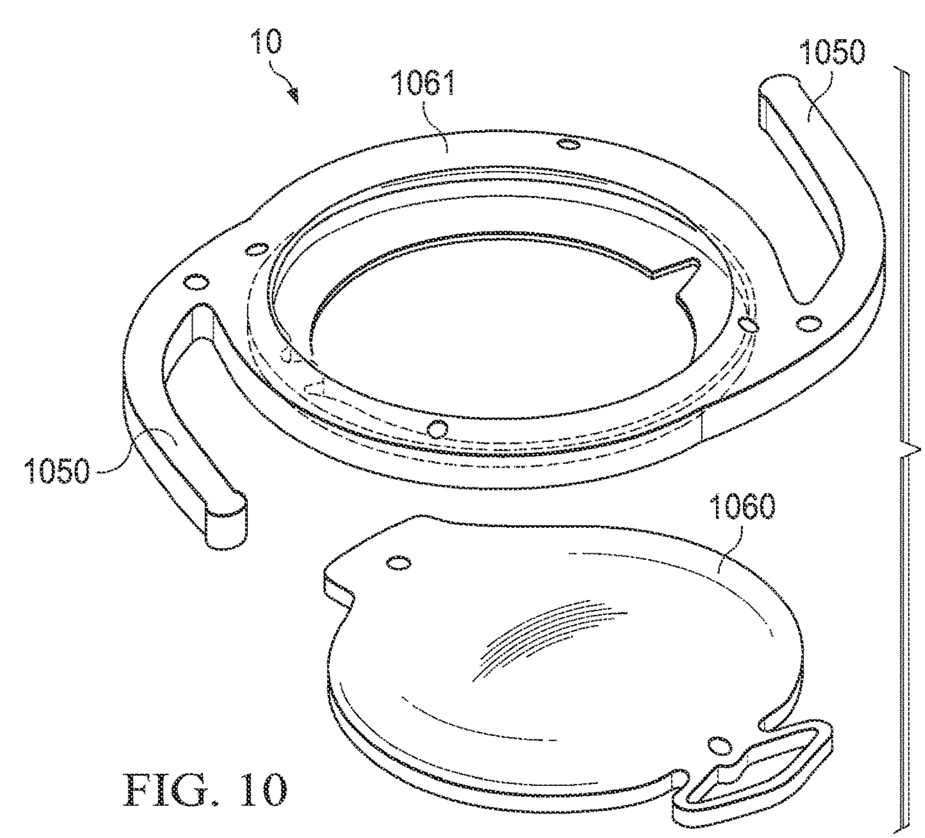
FIG. 10 shows an exemplary two-piece IOL including a base and an optic.

In other implementations, the IOL 10 may be a multi-piece IOL, as shown, for example in FIG. 10. For example, in some implementations, the IOL 10 may include two or more separate components. FIG. 10 is an example IOL 10 that includes two removably attached components. As shown in FIG. 10, the IOL 10 includes an optic 1060 and a base 1061 that includes haptics 1050. The base 1061 may be a hollow base. The optic 1060 and the base 1061 are adapted to be coupled together into a unitary IOL and, thereafter, detached from each other into separate components, if desired. In some instances, one or more components of a multi-piece IOL, such as, for example the two-piece IOL 10 shown in FIG. 10, are separately injectable into a patient's eye. Once in the eye, the components may be assembled into a complete IOL. For example, in the case of the two-piece IOL 10 shown in FIG. 10, the optic 1060 and the base 1061 are separately injectable into an eye. Once injected, the optic 1060 is adapted to be coupled to and to rest on the base 1061.

Figure 2:
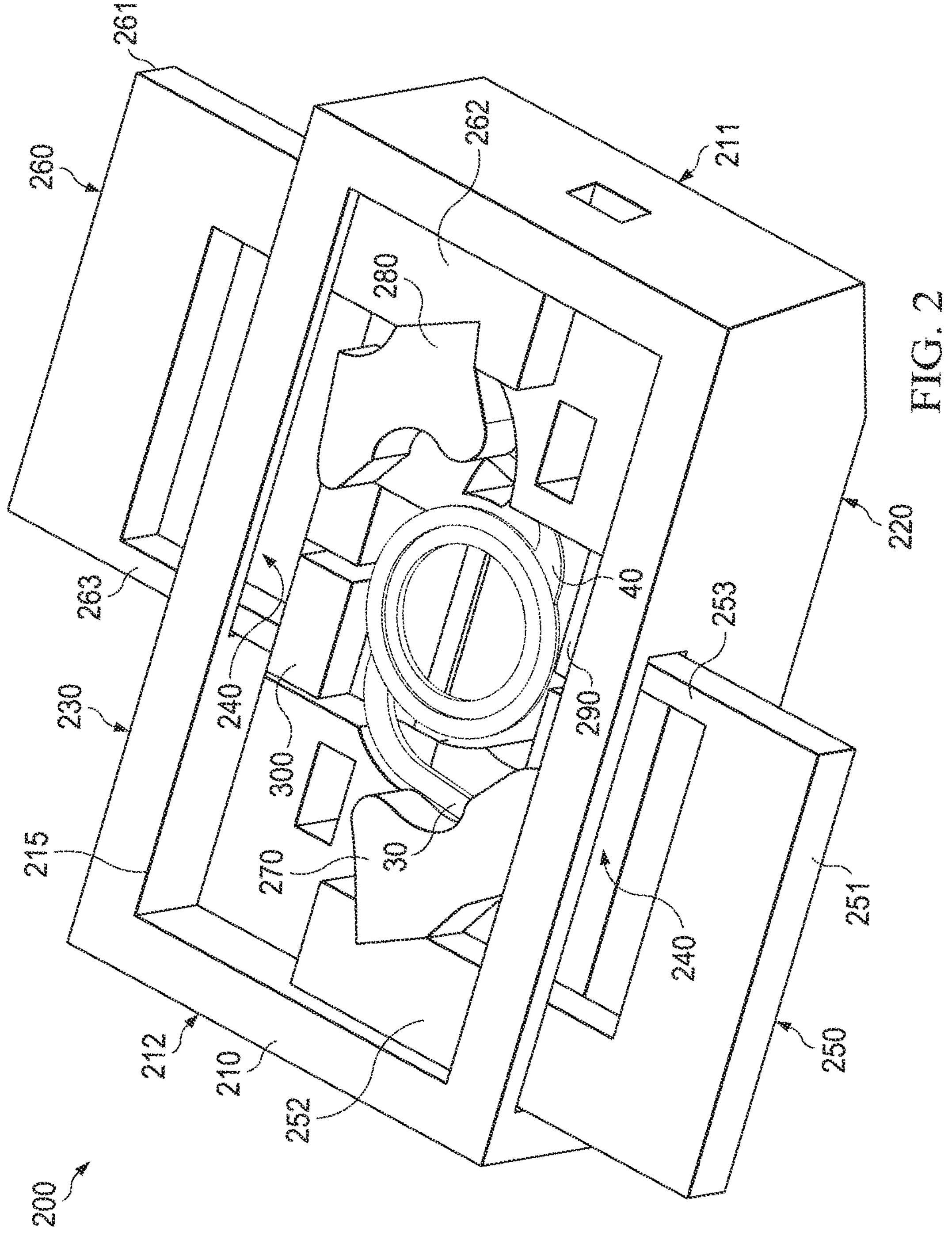
FIG. 2 is a perspective view of an example intraocular lens folding device.
Figure 3:
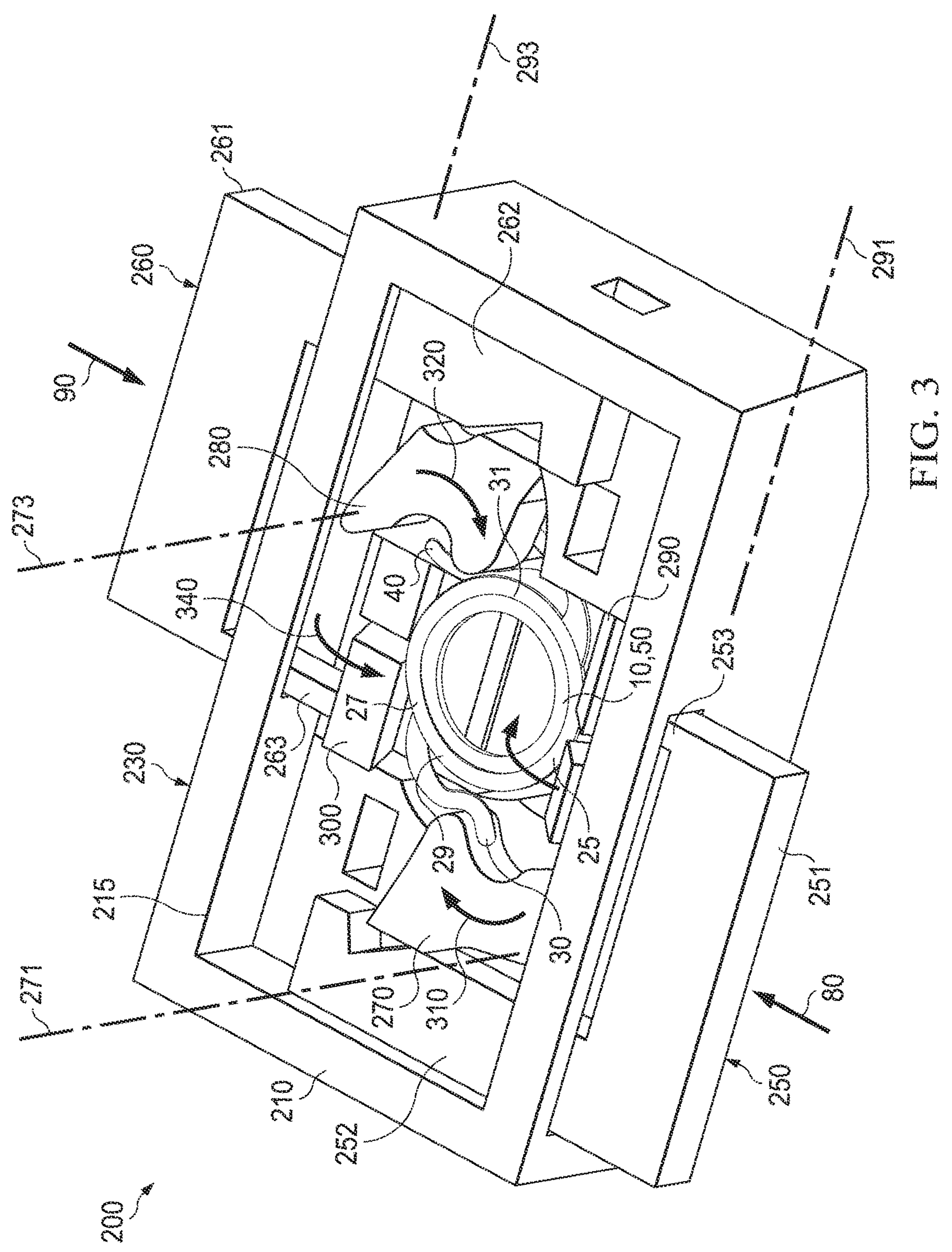
FIG. 3 is a perspective view of the intraocular lens folding device of FIG. 2 in a partially actuated condition.

FIG. 2 shows a perspective view of an example intraocular lens folding device 200 that includes a folding body 210. The folding body 210 includes a first side 220, a second side 230, a distal end 211, and a proximal end 212. Disposed within slots 240 on the first side 220 and second side 230 are a first side actuator 250 and a second side actuator 260. The first side actuator 250 and the second side actuator 260 are moveable into to the folding body 210 through the slots 240. For example, in some instances, the first side actuator 250 and the second side actuator 260 may be moved by the fingers of a user to fold the intraocular lens 10, as shown in FIG. 3. In other implementations, the first side actuator 250 and the second side actuator 260 may be actuated by a separate mechanism, such as a cam, for example.

The first side actuator 250 is disposed within and extends horizontally through the slot 240 on the first side 220 of the folding body 210. The first side actuator 250 includes a contact surface 251 configured for application of manual force by a user to push the first side actuator 250 through the slot 240 into the folding body 210. The first side actuator 250 further includes a first link 252 adapted to engage a first lever 270 rotatably disposed within the folding body 210. The first side actuator 250 also includes a third link 253. The third link 253 is configured to engage a third lever 290 that is disposed within the folding body 210. In the illustrated example, the first link 252 and the third link 253 of the first side actuator 250 extends horizontally through the slot 240 extending through the first side 220 of the folding body.

The second side actuator 260 is disposed within and extends horizontally through the slot 240 formed in the second side 230 of the folding body 210. The second side actuator 260 includes a contact surface 261 configured for application of manual force by a user to push the second side actuator 260 through the slot 240 into the folding body 210. The second side actuator 260 further includes a second link 262 adapted to engage a second lever 280 rotatably disposed within the folding body 210. The second side actuator 260 also includes a fourth link 263 configured to engage with a fourth lever 300 disposed within the folding body 210. Each link of the second side actuator 260 extends horizontally through the slot 240 extending through the second side 230 of the folding body 210.

Figure 4:
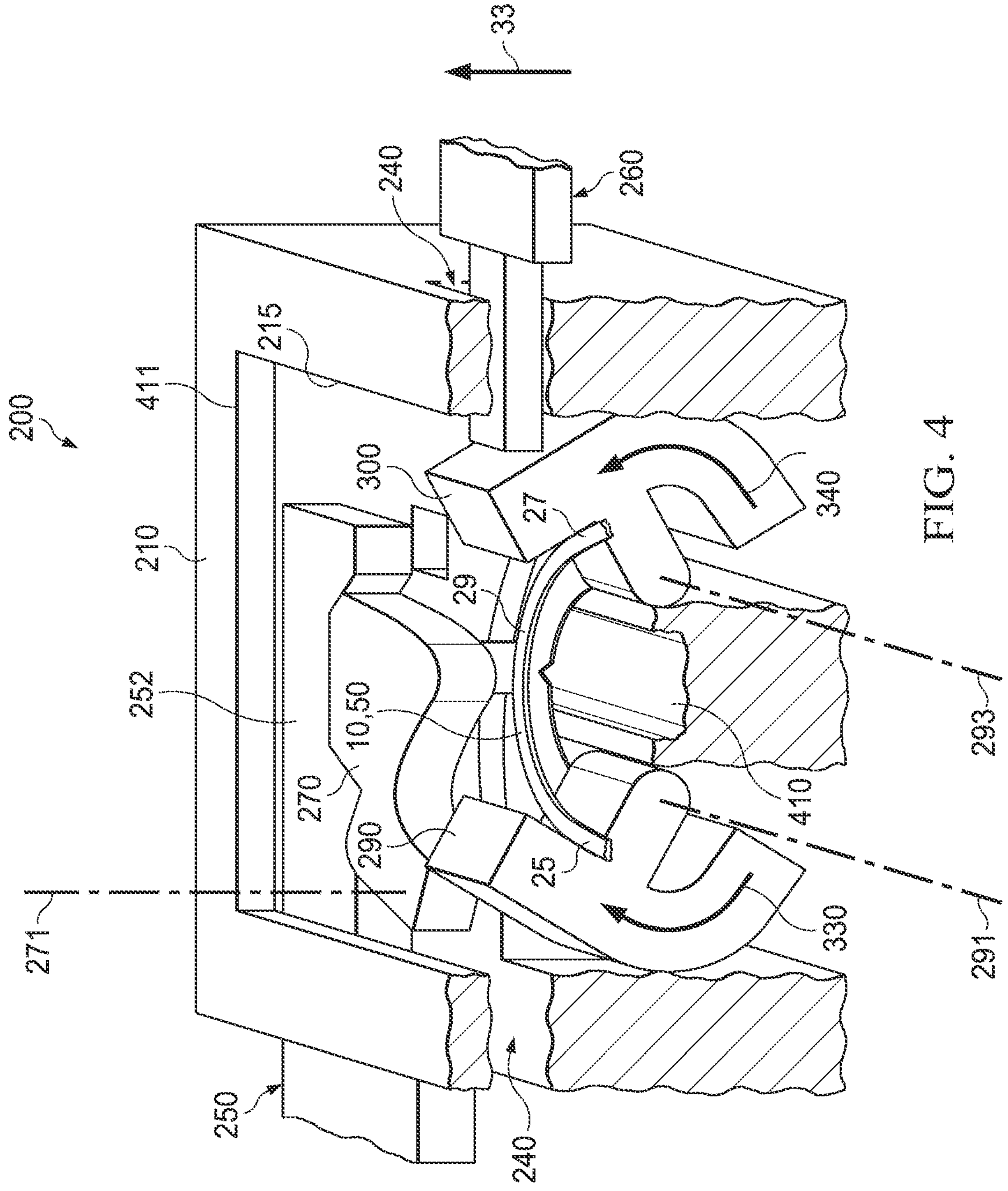
FIG. 4 is a cross-sectional view of the intraocular lens folding device of FIG. 2.

As shown in FIGS. 2-4, the folding body 210 includes a center compartment 215 configured to house an IOL or IOL component (interchangeably referred to as "IOL" 10). The first lever 270 and a second lever 280 are each positioned within the folding body 210 on opposite sides of the center compartment 215. The first lever 270 is in contact with a haptic of an IOL 10 when the IOL 10 is loaded into the center compartment 215 of the folding body 210. In some implementations, the first lever 270 is in contact with the leading haptic 30 when the IOL 10 is loaded into the center compartment 215 of the folding body 210. The second lever 280 is in also contact with a haptic of the IOL 10 when the IOL 10 is loaded into the center compartment 215 of the folding body 210. In some implementations, the second lever 280 is in contact with the trailing haptic 40 when the IOL 10 is loaded into the center compartment 215 of the folding body 210.

As shown in FIGS. 3-4, a user can apply force in direction of arrow 80 to the contact surface 251 of the first side actuator 250 to push the first side actuator 250 through slot 240 into the folding body 210. Likewise, a user can apply force in direction 90 to the contact surface 261 of the second side actuator 260 to push the second side actuator 260 through slot 240 into the folding body 210. When a user pushes the first and second side actuators 250, 260 through the slots 240, the first and second links 252, 262 of the first and second side actuators 250, 260 engage the first and second levers 270, 280 respectively. When engaged by the first link 252 of the first side actuator 250, the first lever 270 rotates in a horizontal plane about a vertical axis 271 in the direction of arrow 310. As a result, the first lever 270 applies a force against the leading haptic 30 to press the leading haptic 30 against the base 50 of IOL 10. IOL 10 as illustrated in FIGS. 3-6 and 11-12 has a hollow base 50, with attached or integrally formed haptics 30 and 40, and including inner portions 29 and 31. When engaged by the second link 262 of the second side actuator 260, the second lever 280 rotates about a vertical axis 273 in the same horizontal plane as the first lever 270 in the direction of arrow 320. The vertical axes 271 and 273 may be parallel to each other. As a result, the second lever 280 applies a force against the trailing haptic 40 to press the leading haptic 40 against the base 50. Thus, the haptics 30, 40 are pushed to make contact with the outer edge of the base 50 in order to fold them into a configuration for implantation into the eye.

As shown in FIGS. 2-4, the third lever 290 is disposed adjacent to the first side 220, and the fourth lever 300 is disposed adjacent to the second side 230. The third and fourth levers 290 and 300 are disposed opposite one another on opposite sides of the center compartment 215. In an unactuated position, the third lever 290 contacts an edge 25 of the base 50, and the fourth lever 300 contacts an edge 27 of the base 50 when the IOL 10 is loaded in the center compartment 215 of the folding body 210. When a user pushes the first and second side actuators 250, 260 through the slots 240, the third and fourth links 253, 263 of the first and second side actuators 250, 260 engage the third and fourth levers 290, 300, respectively. When engaged by the third link 253 of the first side actuator 250, the third lever 290 is rotated about a longitudinal axis 291 in the direction of arrow 330, to press against the edge 25 of base 50, and fold the base 50 into a delivery configuration. When engaged by the fourth link 263 of the second side actuator 260, the fourth lever 300 is rotated about a longitudinal axis 293 in the direction of arrow 340, to press against the edge 27 of base 50, and fold the base 50 into a delivery configuration. The longitudinal axes 291 and 293 may be parallel to each other. One or both of the longitudinal aces 291 and 293 may be perpendicular to one or both of the axes 271 and 273.

FIG. 4 is a cross-sectional view of the intraocular lens folding device 200. FIG. 4 shows the third and fourth levers 290 and 300 being rotated in the course of actuation of the intraocular lens folding device 200. As shown, the third and fourth levers 290, 300 rotate about axes 291 and 293 in directions 330 and 340, respectively, to fold the base 50. The IOL 10 can be folded into a delivery configuration by pressing the edges 25, 27 of the base 50 toward each other and toward the center of the IOL 10, while the inner portions 29 and 31 of the base 50 (as shown in FIGS. 3 and 4) are pressed toward a delivery channel 410. Thus, when folded, the base 50 forms a U-shape with the edges 25 and 27 displaced above the inner portions 29 and 31 in the direction of arrows 330 and 340. Each of the first lever 270 and the second lever 280 includes a pivot pin that is rotatably received into the folding body 210. The first lever 270 and second lever 280 rotate about the vertical axes 271 and 273, respectively, on the pivot pins. The third and fourth levers 290, 300 rotate on pivot pins about coupled to the folding body 210 about longitudinal axes 291 and 293, respectively. In some implementations, the first and second links 252, 262 of the first and second actuators 250, 260 may be coupled to the first and second levers 270, 280, respectively, prior to application of force by a user. In some implementations, the third and fourth links 253, 263 of the first and second actuators 250, 260 may not be coupled to the third and fourth levers 290, 300, respectively. In some implementations, upon user application of force to push the first and second actuators 250, 260 into the folding body 210, the third and fourth links 253, 263 of the first and second actuators 250, 260 may not engage with the third and fourth levers 290, 300 until the third and fourth links 253 and 263 have moved a predetermined distance. Thus, in some implementations, a gap may exist between inboard ends of the third and fourth links 253 and 263 and the third and fourth levers 290 and 300, respectively. Thus, the third and fourth levers 290 and 300 begin to rotate once the third and fourth links 253 and 263 have traversed the gap and engage the third and fourth levers 290 and 300, respectively.

In the illustrated example, the delivery channel 410 is disposed in a lower portion the folding body 210 opposite opening 411. The delivery channel 410 extends from the proximal end 212 to the distal end 211 of the folding body 210. In some implementations, the delivery channel 410 may be aligned with a channel in a body of an IOL injector. The delivery channel 410 can also be configured to align with a delivery channel in a nozzle of an IOL injector, such as a nozzle disposed at a distal end of an IOL injector as shown, for example, in FIGS. 7 and 8. Once the IOL 10 has been folded into the delivery configuration, the IOL 10 is pushed down into the delivery channel 410 for implantation into the eye by an IOL injector. For example, in some implementations, a plunger of an IOL injector may be advanced to engage the folded IOL 10 and advance the IOL 10 through a nozzle and into an eye of a patient. In some implementations, upon application of force by the user to the first and second side actuators 250, 260, causing rotation of the third and fourth levers 290, 300, the third and fourth levers 290, 300 close over the IOL 10, and push the IOL 10 in the folded configuration into the delivery channel 410. As a result, the folded IOL 10 is now disposed between the closed third and fourth levers 290, 300 and the delivery channel 410.

The first and second side actuators 250, 260 may immediately engage the first and second levers 270, 280 upon engagement of the first and second side actuators 250, 260 by the user. The first and second side actuators 250, 260 also immediately engage the third and fourth levers 290, 300 when the user engages the first and second side actuators 250, 260.

In some implementations, the first and second side actuators 250, 260 may engage the first and second levers 270, 280 prior to engaging the third and fourth levers 290, 300. That is, the first and second side actuators 250, 260 may be displaced laterally within the slots 240 a selected distance in response to engagement by a user and displace the first and second lever 270 and 270 before the first and second side actuators 250, 260 begin to actuate the third and fourth levers 290 and 30. This sequential actuation of the levers may ensure that the haptics 30, 40 are pressed against the base 50 of the IOL 10 before the base 50 is folded into the delivery configuration.

An IOL 10 can be preloaded into the folding device 200 prior to shipment to a user, thereby obviating the need for the user to insert the IOL 10 into the folding device 200. This avoids the risk of contamination of the IOL 10 and ensures that the IOL 10 remains sterile throughout the folding process prior to implantation. Furthermore, preloading the IOL 10 reduces the likelihood that the IOL 10 will be damaged during loading into the folding device 200 and/or injector.

Figure 7:
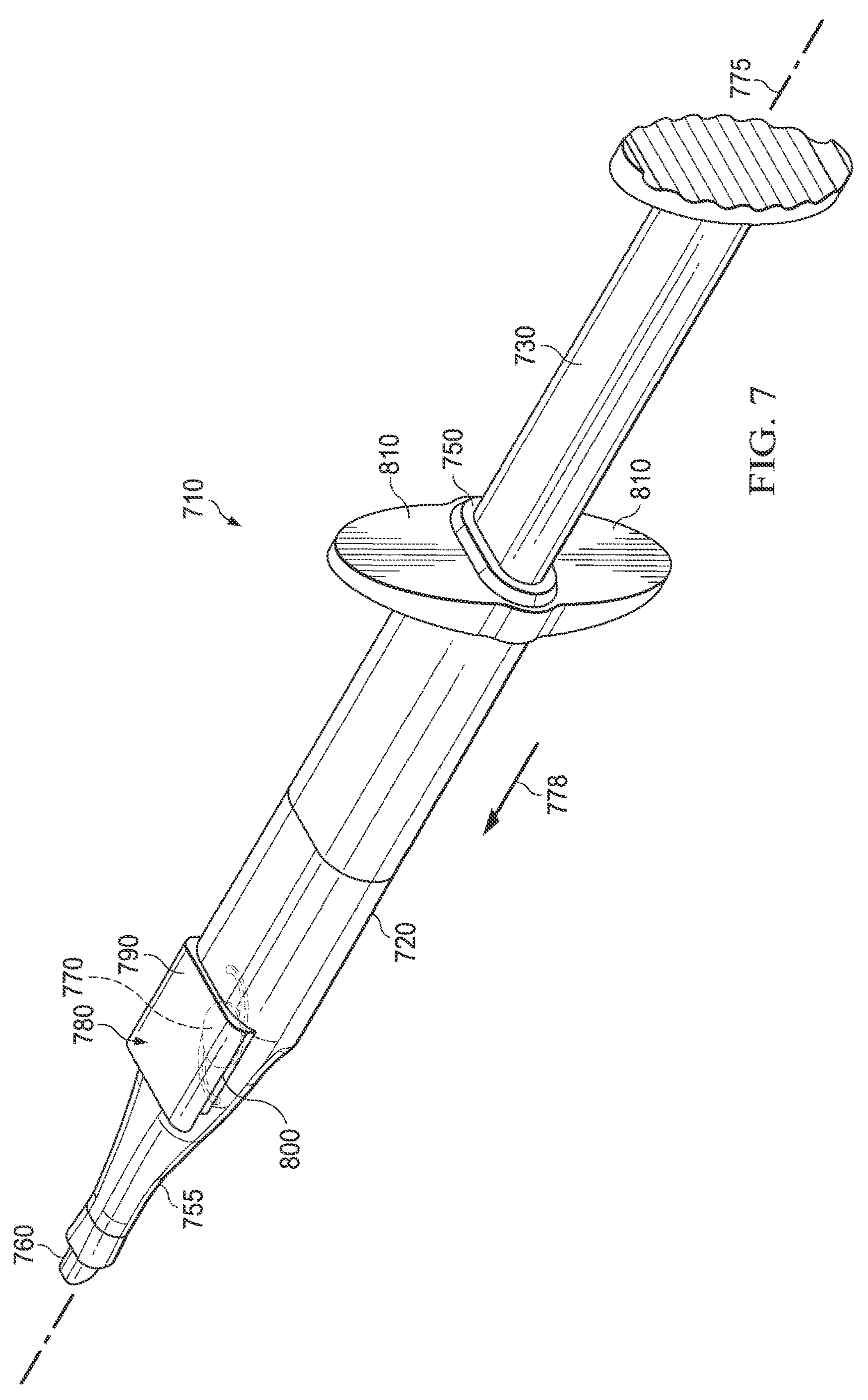
FIG. 7 is a perspective view of an example intraocular lens injector.
Figure 8:
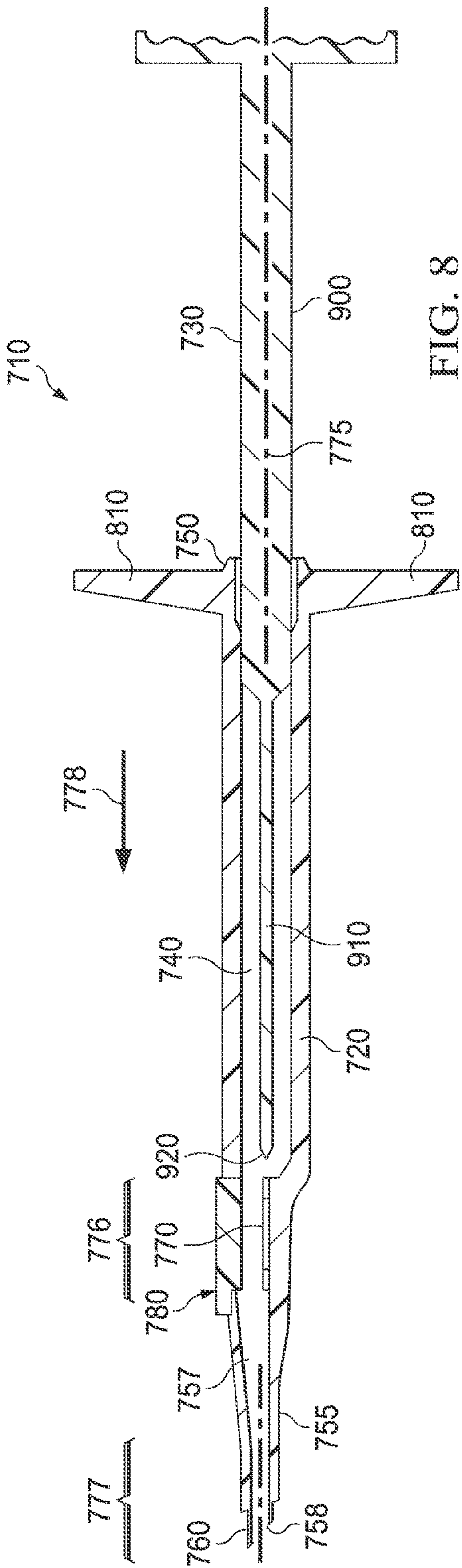
FIG. 8 is a longitudinal cross-sectional view of the intraocular lens injector of FIG. 7.

In some implementations, the folding device 200 may be included in an IOL injector. An example IOL injector that includes a folding device is shown in FIGS. 7 and 8. The example IOL injector shown in FIGS. 7 and 8 may also be a single-use disposable device. Such a device allows the user to fold and implant an IOL with a single, disposable device. In some implementations, an IOL injector may include an injector body, a plunger adapted to reciprocate through the injector body, and a nozzle disposed at the distal end of the injector body. The folding device 200 may be disposed at the proximal end of the nozzle.

Figure 5:
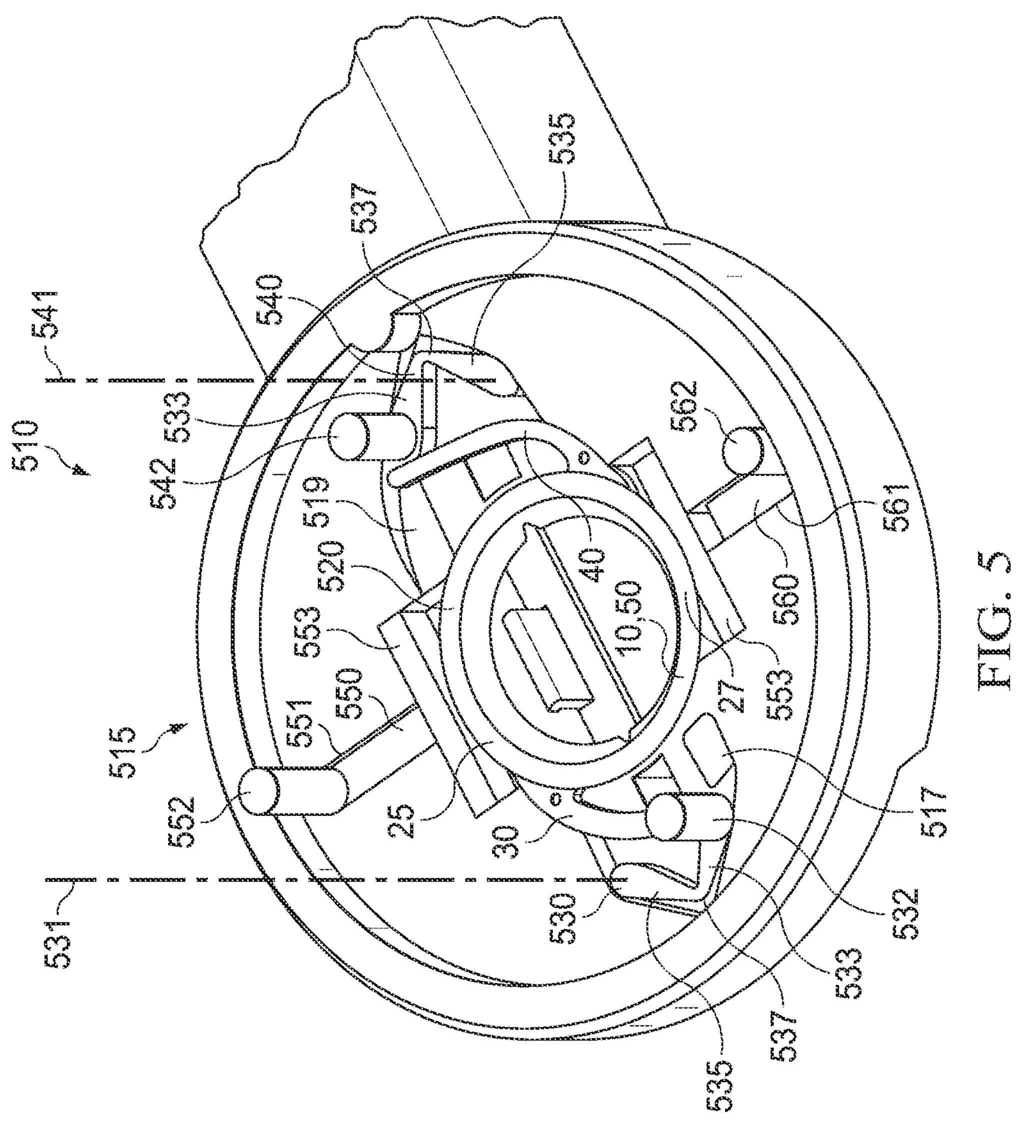
FIG. 5 is a perspective view of another example intraocular lens folding device.
Figure 6:
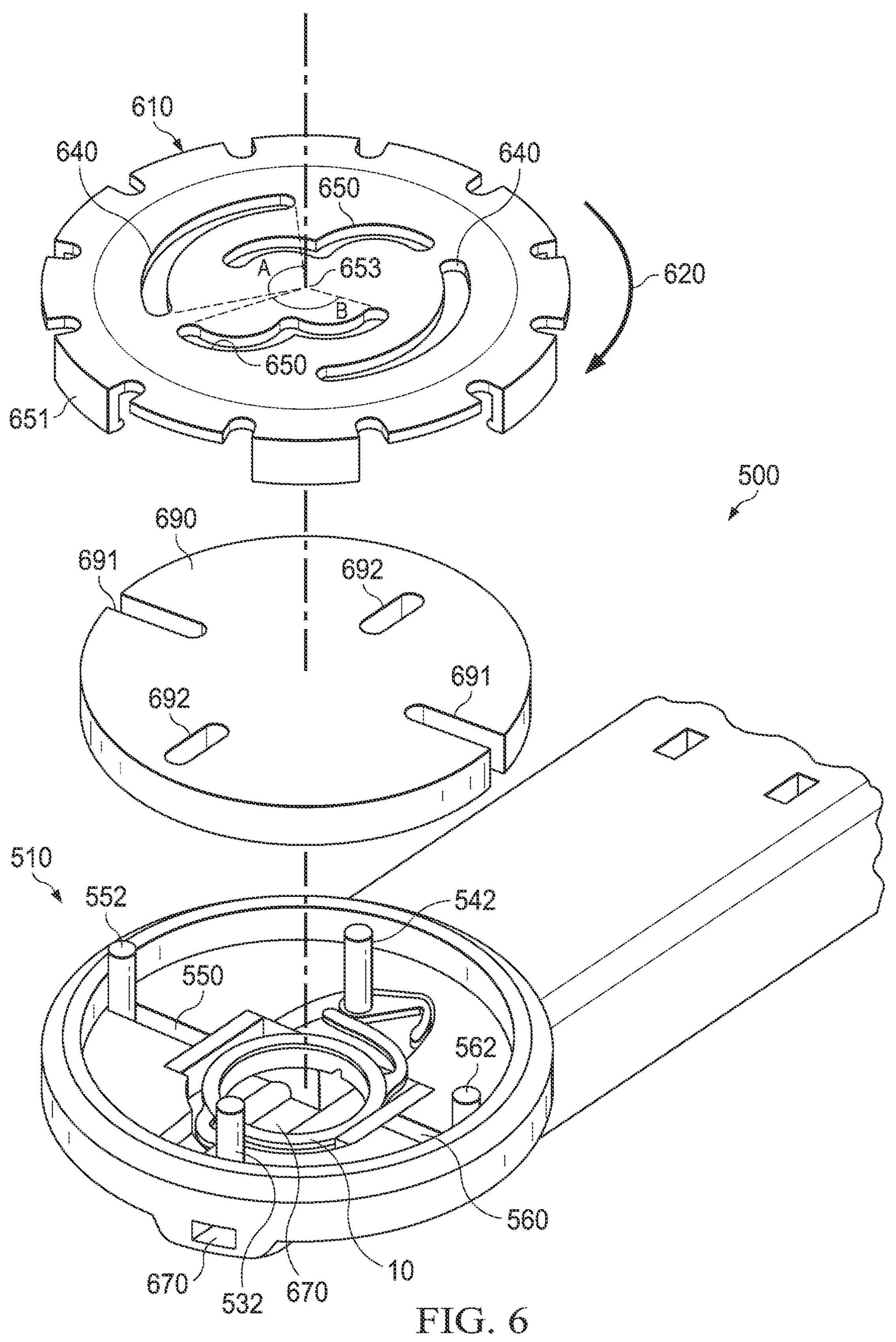
FIG. 6 is an exploded view of the intraocular lens folding device of FIG. 5 that shows an alignment guide and rotatable cover.

FIGS. 5 and 6 show another example folding device 500. The folding device 500 includes a circular folding body 510, which has a center compartment 520 adapted to hold an IOL 10. As above, the IOL 10 includes a leading haptic 30, a trailing haptic 40, and a base 50. A first lever 530, a second lever 540, a third lever 550 and a fourth lever 560 are disposed in and movable within the folding body 510. The first lever 530 and the second lever 540 have pinned connection with folding body 510 such that the first and second levers 530, 540 are pivotable about vertical axes 531 and 541, respectively. Each of the first lever 530 and the second lever 540 includes a first portion 533 and a second portion 535 and a living hinge 537 disposed therebetween. The first portion 533 and the second portion 535 are pivotable relative to each other about the living hinge 537. In operation, the first and second levers 530 and 540 are operable to pivot about both the pinned connections with respect to the folding body 510 and also internally about the living hinges 537 as the pegs 532 and 542 and the corresponding end of the first portion 533 of the levers 530 and 540 move linearly along slots 692, described in more detail below. The third lever 550 and the fourth lever 560 are disposed in slots 551 and 561, respectively, and are translatable therein. The third lever 550 and the fourth lever 560 include walls 553 disposed on inboard ends thereof. The walls 553 are adapted to engage opposing edges of an IOL and press the edges towards each other during actuation of the third and fourth levers 550 and 560. The first lever 530 includes a vertically extending peg 532, and the second lever 540 includes a vertically extending peg 542. The third lever 550 and the fourth lever 560 include vertically extending pegs 552 and 562, respectively.

As shown in FIGS. 5 and 6, the folding device 500 may further include a rotatable cover 610 that is disposed over the center compartment 520 and an alignment guide 690 that is disposed between the folding body 510 and rotatable cover 610. The rotatable cover 610 includes first slots 640 and second slots 650. The alignment guide 690 includes third slots 691 and fourth slots 692. The first slots 640 and the third slots 691 operate in conjunction with the first levers 530 and 540 to actuate the first and second levers 530 and 540. Similarly, the second slots 650 and the fourth slots 692 operate in conjunction with the third lever 550 and the fourth lever 560 to actuate the third and fourth levers 550 and 560. The rotatable cover 610 is rotatable in the direction of arrow 620 to actuate the folding device 500 and fold IOL 10. The rotatable cover 610 can be rotated by a user applied force. The alignment guide 690 is stationary with respect to the folding body 510. Thus, the rotatable cover 610 is also rotatable relative to the alignment guide 690 and the folding body 510. As explained below, the alignment guide 690 and the rotatable cover 610 work together with the first and second levers 530 and 540 and with the third and fourth levers 550 and 560 to fold IOL 10.

As shown in FIGS. 5 and 6, the first slots 640 are in the form of an arc having a first end adjacent to an outer perimeter 651 of the rotatable cover 610 and converging towards a center 653 thereof over an angle A. The second slots 650 are in the form of a serpentine shape. The second slots 650 extend from a position adjacent to the outer perimeter 651 of the rotatable cover 610 and converge towards the center 653 of the rotatable cover 610 over an angle B. In the illustrated example, the angles A and B are 90°, thereby limiting an amount by which the rotatable cover 610 may be rotated. However, in other implementations, the angles A and B may be greater than or less than 90°.

Each of the pegs 532 and 542 of the first and second levers 530 and 540, respectively, extends through one of the fourth slots 640 and one of the second slots 450. Each of the pegs 552 and 526 of the third and fourth levers 550 and 560, respectively, extend through one of the first slots 640 and one of the third slots 691. The slots 691 and 692 formed in the alignment guide constrain movement of the pegs disposed therein in a radial direction. Particularly, as described below in the context of the illustrated example, rotation of the rotatable cover 610 causes the pegs 532, 542, 552, and 562 to move inwards towards the center of the folding body along the corresponding third and fourths slots 691 and 692. For a given rate of rotation of the rotatable cover 610, the first and second slots 640 and 650 define how the first lever 530 and second lever 540 move relative to the third lever 550 and fourth lever 560 along their respective slots 691 and 692 formed in the alignment guide 690 and the rates at which the levers move.

In the illustrated example, the first slots 640 and the second slots 650 formed in the rotatable cover 610 and the third slots 691 and the fourth slots 692 formed in the alignment guide 690 are arranged in a pattern so as to cause symmetrical action of the first and second levers 530 and 540 and symmetrical action of the third and fourth levers 550 and 560 so as to cause symmetrical folding of IOL 10. At an initial position, the first, second, third, and fourth levers 530, 540, 550, and 560 are arranged adjacent to an outer edge 515 of the folding body. When an IOL 10 is loaded into the center compartment 520 of the folding body 510, the first lever 530 is in contact with the leading haptic 30 and the second lever 530 is in contact with the trailing haptic 40. Similarly, with the IOL 10 loaded into the compartment 520, the third and fourth levers 550 and 560 are in contact with opposing edges 25 and 27 of the base 50.

As the rotatable cover 610 rotates, the second slots 650, in combination with the third slots 691, interact with pegs 532 and 542 of the first and second levers 530 and 540, respectively, to cause both to pivot inwardly towards the center of the folding body 510 as well as about living hinges 537 to fold the leading and trailing haptics 30 and 40 inwardly towards the base 50 of the IOL. The third and fourth pegs 552 and 562 interact with the first slots 640 and the third slots 691 to cause the third and fourth levers 550 and 560 to advance towards the center of the folding body 510 at a slower rate than the first and second levers 530 and 540 due to the nature of the first slots 640. As the third and fourth levers 550 and 560 are actuated, opposing sides of the base 50 of the IOL are forced towards each other to fold the IOL 10.

During folding, the leading and trailing haptics 30 and 40 are folded so as to press against the base 50. With the leading and trailing haptics 30 and 40 folded, the third and fourth levers 550 and 560 press against opposing edges of the base 50 to fold the base 50 and the haptics 30 and 40 such that the folded IOL 10 drops into a delivery channel 670 within the folding body 510. Once disposed in the delivery channel 670, a plunger may be advanced to drive the folded IOL 10 out of the folding device 500 and into, for example, a nozzle of an IOL injector. The folding device 500 may fold the IOL 10 into a delivery configuration. As a result of the cooperating slots of the rotatable cover 610 and the alignment guide 690, rotational motion of the rotatable cover 610 is converted into linear movement of the levers 530, 540, 550, and 560.

In other implementations, the alignment guide 690 may be omitted, because, in other implementations, the folding body 510 may include grooves along which the levers 530, 540, 550, and 560 follow. For example, in FIG. 5, levers 550 and 560 are received into slots 551 and 561, respectively, that constrain movement of the levers 550 and 560 in linear, radial directions. Similarly, slots 517 and 519 may be included in the folding body 510 to constrain the movement of the first and second levers 530 and 540 in linear, radial directions.

Thus, when a user applies a rotational force to the rotatable cover 610, the rotation of the rotatable cover 610 is translated into linear motion as a result of interaction between the pegs 532, 542, 552, and 562 of the levers 530, 540, 550, and 560 and the slots formed in the rotatable cover 610 and alignment guide 690, causing the levers 530, 540, 550, and 560 to apply the forces to the IOL 10 to fold the IOL 10 into the delivery configuration. In some implementations, the first and second levers 530, 540 begin moving inwardly at the instant the rotatable cover 610 begins to rotate. The slots 640 and 650 formed in the rotatable cover 610 may be configured such that the first and second levers 530, 540 are delayed from advancing inwardly for a given amount of angular rotation of the rotatable cover 610. In some implementations, the third and fourth levers 550, 560 being moving inwardly at the instant the rotatable cover 610 begins to rotate. In other implementations, the slots 650, 660 formed in the rotatable cover 610 may be configured such that the third and fourth levers 550, 560 are delayed from advancing inwardly for a given amount of angular rotation of the rotatable cover 610.

In some implementations, the first and second levers 530, 540 advance prior to the third and fourth levers 550, 560 in response to rotation of the rotatable cover 610. This sequential motion may ensure that the haptics 30, 40 are pressed against the base 20 of the IOL 10 before the base 20 is folded into the delivery configuration.

As explained above, once the IOL 10 has been folded into the delivery configuration, the IOL 10 may be pushed along the delivery channel 670 by a plunger prior to implantation into an eye. The delivery channel 670 may extend from a proximal end to a distal end of the folding body 510. The delivery channel 670 may be configured to align with a channel formed in a body of an IOL injector. The delivery channel 670 may also be configured to align with a delivery channel in a nozzle of an IOL injector.

Once the IOL 10 has been folded into the delivery configuration, the IOL 10 may be pushed down into the delivery channel 670 for implantation into the eye. In some implementations, upon rotation of the rotatable cover 610 by a user, the third and fourth levers 550, 560 and the third and fourth levers 550, 560 converge towards the center of compartment 520 and push the IOL 10 in the folded configuration. The folded IOL 10 then drops into the delivery channel 670 and is ready for further advancement by a plunger, for example.

In some implementations, the IOL 10 may be preloaded into the folding device 500. Having the IOL 10 preloaded may ensure that the IOL 10 remains sterile throughout the folding process prior to implantation. Furthermore, preloading the IOL 10 may reduce the risk that the IOL 10 will be damaged during loading into the folding device and/or injector.

Figure 11:
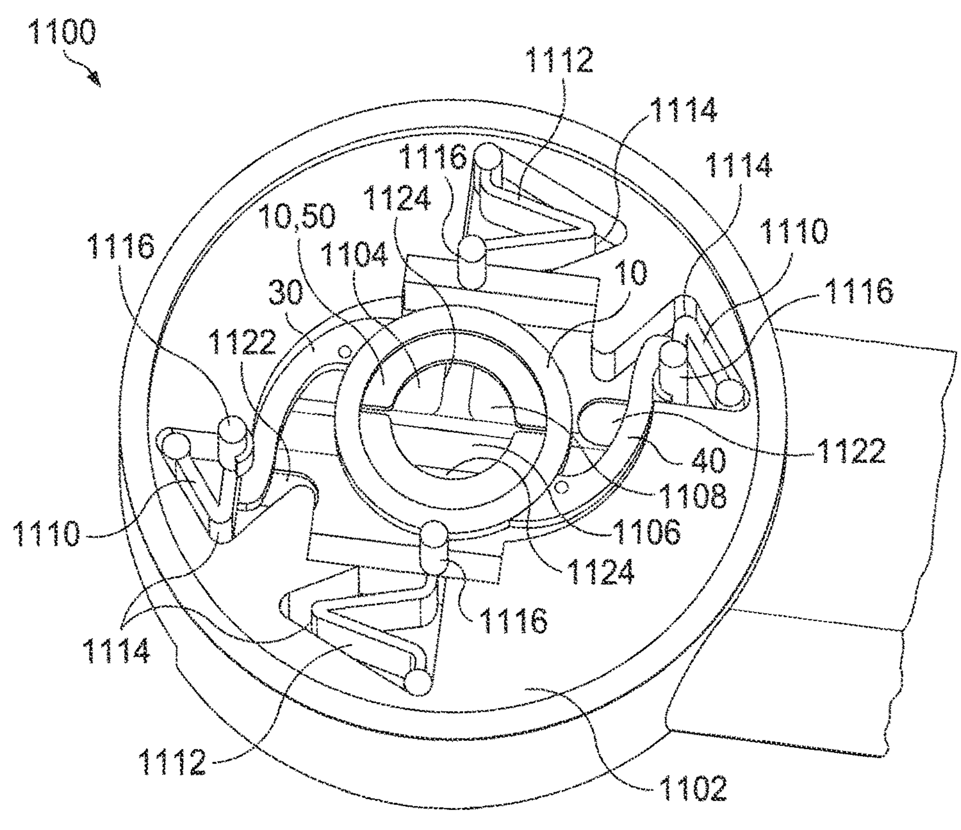
FIG. 11 is a perspective view of another example intraocular lens folding device.
Figure 12:
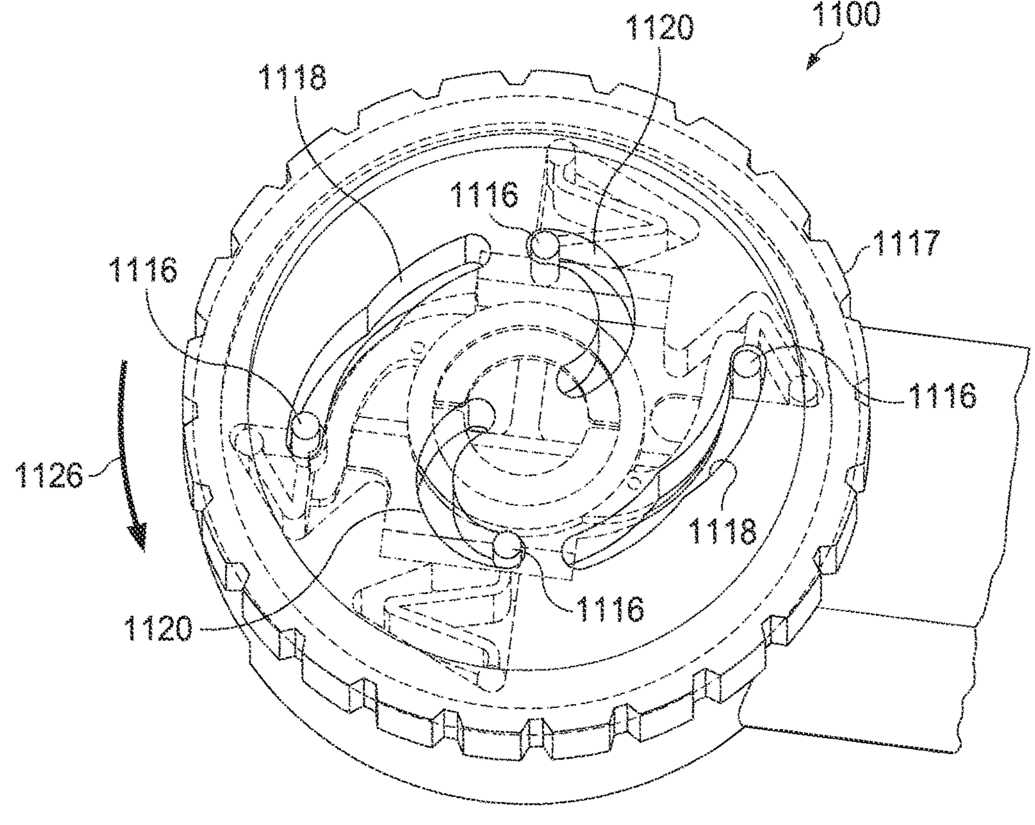
FIG. 12 is a perspective view of the example intraocular lens folding device of FIG. 11 with a top rotatable cover.

Another example folding device 1100 is shown in FIGS. 11-12. The folding device 1100 operates in a similar manner as the folding device 500 described above. For example, as with the folding device 500, the folding device 1100 includes a folding body 1102 that defines a central compartment 1104 adapted to receive an IOL 10. A delivery channel 1106 is formed in a floor 1108 of the central compartment 1104. The delivery channel 1106 is adapted to transport a folded IOL once folded by the folding device 1100 into a delivery configuration.

The folding device 1100 also includes two sets of levers 1110 and 1112. The levers 1110 are similar to the first and second levers 530 and 540, while the levers 1112 are similar to the third and fourth levers 550 and 560. In this example, all of the levers 1110 and 1112 include a living hinge 1114 that permits the levers 1110 and 1112 to extend as the hinges 1114 allow the levers to unfold from an initial folded configuration, as shown in FIG. 11, as the levers 1110 and 1112 are advanced towards a center of the central compartment 1104. Each of the levers 1110 and 1112 includes a peg 1116 extending vertically therefrom.

The folding device 1100 also includes a rotatable cover 1117 that includes first slots 1118 that receive the pegs 1116 for the levers 1110 and second slots 1120 that receive the pegs 1116 of the levers 1112. The folding device 1110, though, omits a separate alignment guide. Rather, slots 1122 and 1124 may be formed in the folding body 1102 that receive levers 1110 and 1112, respectively. The slots 1122 and 1124 constrain movement of the levers 1110 and 1112, respectively, in linear, radial directions. Thus, an alignment guide is may be omitted.

The folding device 1100 operates similarly to the folding device 500. The pegs 1116 of the levers 1110 and 1112 are received into the corresponding slots 1118 and 1120 such rotation of the rotatable cover 1117 in the direction of arrow 1126 cause the levers 1110 and 1112 to move along respective slots 1122 and 1124 inwardly to fold IOL 10 in a manner similar to that described above. In some implementations, the slots 1118 and 1120 may be arranged and shaped so as to cause the levers 1110 and levers 1112 to move sequentially. For example, the slots 1118 and 1120 may be configured such that levers 1110 move inwardly before levers 1112 as the rotatable cover 1117 is rotated in the direction of arrow 1126. Sequential movement of the levers 1110 and 1112 may be desirable to fold the haptics 30 and 40 onto the base 50 prior to folding of the base 50.

The folding device 500 may be incorporated into an IOL injector. An example IOL injector 710 is shown in FIGS. 7 and 8. In some instances, the IOL injector 710 may be disposable after a single use or fewer than 5 uses. This allows the user to fold and implant an IOL with a single, disposable device.

FIGS. 7 and 8 are exemplary schematics of an IOL injector 710 that includes an injector body 720, a plunger 730 adapted to reciprocate through a bore 740 formed the injector body 720, and a nozzle 755 disposed at a distal end 760 of the injector body 720. The nozzle 755 defines a passage 757 through which a folded IOL may be advanced and delivered into an eye via opening 758. A delivery channel of folding device 776, which may be the delivery channel 670 of the folding device 500 or delivery channel 1106 of folding device 1100, may be aligned with bore 740 and/or the passage 757. The folding device 776 is shown schematically in FIGS. 7 and 8 with the understanding that folding device 776 may be any folding device within the scope of the present disclosure. The bore 740, the delivery channel of the folding device 776, and the passage 757 may combine and extend from a proximal end 750 of the injector body 720 to a distal end 760 of the injector body 720. The plunger 730 is received within the bore 740 and moveable therein such that the plunger 730 is slideable within the bore 740. Particularly, the plunger 730 is slideable within bore 740 in order to advance an IOL, such as IOL 770, within delivery channel of the folding device 776 and the passage 757 of the nozzle 755.

The IOL injector 710 also includes a longitudinal axis 775. The longitudinal axis 775 may extend along the plunger 730 and define a longitudinal axis of the plunger 730. The folding device 776 may include a storage compartment 780 operable to house an IOL 770 prior to insertion into an eye. In some instances, the folding device 776 may include a door 790 to provide access to the storage compartment 780. The door 790 may include a hinge 800 such that the door 790 may be pivoted about the hinge 800 to open the compartment 780. In other implementations, the folding device 776 may exclude a door for installing the IOL. In such instances, the IOL may be incorporated into the folding device 776 at the time of assembly of the folding device 776. Thus, in such instances, the IOL injector 710 would be a preloaded IOL injector.

The injector body 720 may also include tabs 810 formed at the proximal end 750 of the injector body 720. The tabs 810 may be manipulated by fingers of a user, such as an ophthalmologist or other medical professional, to advance the plunger 730 through the bore 740. The plunger 730 may include a body portion 900, a plunger rod 910 extending distally from the body portion 900, and a plunger tip 920 formed at a distal end of the plunger rod 910 and adapted to contact the folded IOL disposed, for example, within the IOL storage compartment 780 of the folding device 776 of the IOL injector 710. As the plunger 730 is displaced distally within bore 740 in the direction of an arrow 778, the plunger 730 engages and advances the folded IOL, such as IOL 770, contained in the compartment 780.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 10 may be a two-piece IOL, as shown, for example, in FIG. 10. The IOL 10 includes the base 1061 and the optic 1060 are separately injected into the patient's eye. Accordingly, for two-piece IOLs, the base 1061 and the optic 1060 may be contained in separate IOL injectors for insertion in the eye. In other implementations, the two components of a two-piece IOL may be inserted into an eye separately using a single IOL injector. For example, as shown in FIGS. 3-6 and 11-12, the IOL 10 may include a base 50 and haptics 30 and 40, which may be inserted separately from an optic, which will rest in the hollow base. For a single piece IOL (as shown, for example, in FIG. 1), the optic 20 and haptics 30 and 40 form a unitary IOL and is insertable into an eye as a single unit with the use of a single IOL injector.

Accordingly, in some implementations, a user may place a one-piece IOL into an IOL injector, for example, by loading an IOL into the IOL storage compartment of the IOL injector accessed via a door, for example. In some implementations, the IOL may be manually folded into a compressed or folded configuration prior to installation into an IOL injector.

In the case of a two-piece IOL, in some implementations, a user may load the base (which may be similar to base 1061 or base 50) into an IOL storage compartment of an IOL injector, for example, via a door. The optic (which may be similar to optic 1060) may be introduced into the IOL storage compartment of separate IOL injector, for example, via a door. In some instances, the IOL storage compartment may be accessed through the door similar to door 790. In some implementations, one or both of the base and the optic may be manually folded into a compressed or folded configuration prior to installation into an IOL injector.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment of an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed in the IOL injector before and is already contained within the IOL injector when the IOL injector is received by the user. The IOL injector(s) may be packaged within sterile packaging when received by a user.

As would be understood by persons of ordinary skill in the art, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. Manual installation and folding of an IOL may also introduce the possibility of contamination of the IOL, such as by human error or poor sterile technique. Contamination of the IOL may compromise the sterile environment for the patient and risk infection or other harm to the patient.

Figure 9:
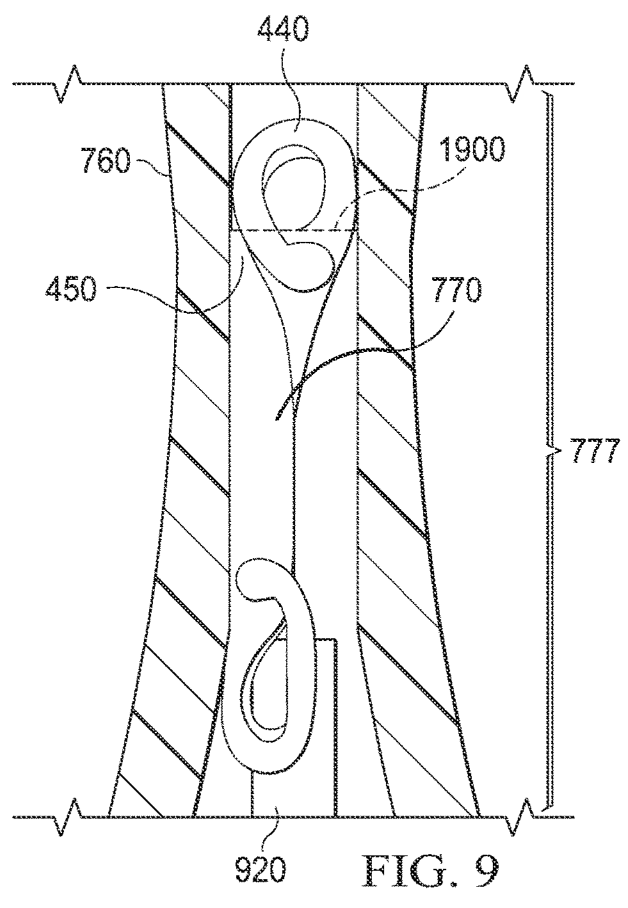
FIG. 9 is a view of a distal end of an IOL injector with an IOL located therein and positioned at a dwell position.

FIG. 9 shows a view of the distal end 760 of the IOL injector with an IOL 770 located therein at a dwell position 777. The dwell position 777 in FIG. 9 may correspond to a dwell position 777 shown in FIG. 8. As shown in FIG. 9, the dwell position of the IOL may be defined as a location where a distal edge of an optic 450 of the IOL 770 substantially aligns with the demarcation 1900. A haptic 440 or a portion thereof may extend beyond the demarcation 1900.

Various implementations of the IOL folding devices described herein and within the scope of the present disclosure may be configured to fold an IOL base and/or an IOL optic of a multi-piece IOL or configured to fold a single-piece IOL. Various implementations of the IOL folding device and associated methods described herein may be used with an IOL base and/or the optic that are manually loaded into the IOL folding device by a user or pre-loaded therein prior to delivery by a user.

Non-limiting examples of IOL injectors that may be adapted for use with the IOL folding device as described herein include those described in U.S. Pat. No. 7,156,854 and U.S. Patent Application Publication No. 2016/0256316, the disclosures of each being incorporated herein by reference in their entireties.

The present disclosure discloses folding devices for components of a multi-piece intraocular lens, including a two-piece IOL. The folding device may be coupled to an intraocular lens injector for implanting the folded component of the multi-piece IOL. The IOL may be folded using user actuated motions to fold the base, the optic, or the base/optic assembly into a delivery configuration during the delivery. In some implementations, the leading and trailing optics are first placed into a delivery configuration and position by pushing and holding the haptics against the ring's outer edge. Then, the ring is folded into the delivery configuration for advancement into the eye for implantation.

In some implementations, the intraocular lens folding device may include a folding body, in which a first side actuator may be disposed within and extends horizontally through a slot on a first side of the folding body. A second side actuator may be disposed within and extend horizontally through a slot on a second side of the folding body. A center compartment of the folding body may be configured to house an IOL. Within the folding body, first and second levers are positioned to contact the haptics of an IOL, and, when a user inputs force on the first and second side actuators, the actuators engages with the first and second levers, causing the levers to rotate and produce a force against the haptics to press the haptics against the base. The folding body may further include third and fourth levers that are adapted to contact the base of the IOL. When a user inputs force on the first and second side actuators, the actuators engage with the third and fourth levers, causing the levers to rotate and produce a force against the base to fold the base into a delivery configuration for delivery.

In another implementation, the intraocular lens folding device may include a circular folding body, including a center compartment configured to house an IOL. A rotatable cover may be disposed over the center compartment. Within the folding body, a first lever can contact a haptic and may have a peg that extends vertically through a first slot in the cover. A second lever may contact the opposite haptic and may have a peg that extends vertically through a second slot in the cover. When a user applies a rotational force to the cover, the cover guides the pegs and the corresponding the first and second levers to apply a force against the haptics to press the haptics against the base. The folding body may further include third and fourth levers. Each of the third and fourth levers may have pegs extending vertically through a third and fourth slot in the cover, respectively. When the cover is rotated by the user, the cover guides the pegs and the third and fourth levers to apply a force against the base to fold the base into a delivery configuration for delivery.

The folding devices disclosed herein avoid direct contact between the IOL and a user in folding the IOL, as the folding devices utilize mechanical linkages to complete the IOL object folding. The use of mechanical linkages reduces the risk of folding errors and reduces the risk of introducing contamination to the components of the folding device and the IOL contained therein throughout folding and injection of the IOL.

Although the disclosure provides numerous examples, the scope of the present disclosure is not so limited. Rather a wide range of modification, change, and substitution is contemplated in the foregoing disclosure. It is understood that such variations may be made to the foregoing without departing from the scope of the present disclosure.

The invention claimed is:

1. An intraocular lens (IOL) injector comprising:
an injector body;
a nozzle having a hollow interior disposed on a distal end of the injector body;
a plunger adapted to reciprocate within the injector body and to contact and apply force to an IOL disposed in the IOL injector, the IOL comprising:
a first haptic;
a second haptic; and
a base comprising a first edge and a second edge; and
a folding body comprising:
a center compartment adapted to house the IOL;
a first lever disposed within the folding body and adapted to contact and apply force against the first haptic of the IOL sufficient to press the first haptic against the base of the IOL;
a second lever disposed within the folding body and adapted to contact and apply force against the second haptic of the IOL sufficient to press the second haptic against the base of the IOL;
a third lever disposed within the folding body and adapted to contact and apply force against the first edge of the IOL base sufficient to fold the base of the IOL;
a fourth lever disposed within the folding body and adapted to contact and apply force against the second edge of the IOL base sufficient to fold the base of the IOL.

2. The IOL injector of claim 1, wherein the folding body further comprises:
a first side comprising a first slot;
a second side disposed opposite the first side and comprising a second slot;
a first side actuator disposed within and extending horizontally through the first slot and comprising:
a first side actuator contact surface adapted for application of manual force;

a first link extending horizontally through the slot on the first side of the folding body, the first link contiguous with the first side actuator contact surface and rotatably coupled to the first lever and adapted to horizontally rotate the first lever in response to application of manual force to the first actuator contact surface to apply force to the first haptic of the IOL sufficient to press the first haptic against the base of the IOL; and a third link extending horizontally through the slot on the first side of the folding body the third link contiguous with the first side actuator contact surface adapted to engage the third lever to vertically rotate the third lever in response to application of manual force to the first actuator contact surface to apply force to the first edge of the IOL sufficient to fold the base of the IOL;

a second side actuator disposed within and extending horizontally through the second slot and comprising:

a second side actuator contact surface adapted for application of manual force;

a second link extending horizontally through the slot on the second side of the folding body, the second link contiguous with the second side actuator contact surface and rotatably coupled to the second lever and adapted to horizontally rotate the second lever in response to application of manual force to the second actuator contact surface to apply force to the second haptic of the IOL sufficient to press the second haptic against the base of the IOL; and a third link extending horizontally through the slot on the second side of the folding body the third link contiguous with the second side actuator contact surface adapted to engage the fourth lever to vertically rotate the fourth lever in response to application of manual force to the second actuator contact surface to apply force to the second edge of the IOL sufficient to fold the base of the IOL.

3. The IOL injector of claim 2, wherein the first and second links rotate the first and second levers prior to the third and fourth links engaging the third and fourth levers.

4. The IOL injector of claim 2, wherein the first side actuator and the second side actuator are adapted for simultaneous application of manual force.

5. The IOL injector of claim 1, wherein the folding body is a circular folding body and further comprises a rotatable cover disposed over the center compartment of the folding body, the rotatable cover comprising a first slot, a second slot, a third slot, and a fourth slot, wherein:

the first lever is disposed within the circular folding body and comprises a first peg extending through the first slot and a first pivot point, the first lever is adapted for, when the rotatable cover is rotated, the first peg to slidingly interact with the first slot to rotate the first lever around the first pivot point to contact and apply force to the first haptic of the IOL sufficient to press the first haptic against the base of the IOL;

the second lever is disposed within the circular folding body and comprises a second peg extending through the second slot and a second pivot point, the second lever is adapted for, when the rotatable cover is rotated, the second peg to slidingly interact with the second slot to rotate the second lever around the second pivot point to contact and apply force to the second haptic of the IOL sufficient to press the second haptic against the base of the IOL;

the third lever is disposed within the circular folding body and comprises a third peg extending through the third slot and a third pivot point, the third lever is adapted for, when the rotatable cover is rotated, the third peg to slidingly interact with the third slot to rotate the third lever around the third pivot point to contact and apply force to the first edge of the IOL sufficient to fold the base of the IOL; and the fourth lever is disposed within the circular folding body and comprises a fourth peg extending through the fourth slot and a fourth pivot point, the fourth lever is adapted for, when the rotatable cover is rotated, the fourth peg to slidingly interact with the fourth slot to rotate the fourth lever around the fourth pivot point to contact and apply force to the second edge of the IOL sufficient to fold the base of the IOL.

6. The IOL injector of claim 5, wherein the circular folding body further comprises a second rotatable cover disposed above and coupled to the first rotatable cover.

7. The IOL injector of claim 6, wherein the injector body further comprises a delivery channel disposed below the folding body and extending from a proximal end of the folding body to a distal end of the folding body, the delivery channel adapted to receive an IOL folded into a delivery configuration for delivery and align with a delivery channel in the injector body and nozzle.

8. The IOL injector of claim 6, further comprising the IOL disposed within the center compartment.

9. The IOL injector of claim 8, wherein the IOL further comprises an optic disposed within the base.

* * * * *